US00PP29195P3

(12) United States Plant Patent
Hansen

(10) Patent No.: US PP29,195 P3
(45) Date of Patent: Apr. 3, 2018

(54) ***×MANGAVE* PLANT NAMED 'MOONGLOW'**

(50) Latin Name: ***×Mangave×Manfreda* hybrid**
Varietal Denomination: Moonglow

(71) Applicant: Hans A. Hansen, Zeeland, MI (US)

(72) Inventor: Hans A. Hansen, Zeeland, MI (US)

(73) Assignee: Walters Gardens, Inc, Zeeland, MI (US)

( * ) Notice: Subject to any disclaimer, the term of this patent is extended or adjusted under 35 U.S.C. 154(b) by 0 days.

(21) Appl. No.: 15/330,178

(22) Filed: Aug. 18, 2016

(65) Prior Publication Data

US 2018/0054944 P1 Feb. 22, 2018

(51) Int. Cl.
*A01H 5/02* (2006.01)
*A01H 5/12* (2018.01)

(52) U.S. Cl.
USPC ..... Plt./373
CPC ..... *A01H 5/12* (2013.01)

(58) Field of Classification Search
USPC ..... Plt./373
See application file for complete search history.

(56) References Cited

PUBLICATIONS

Avent, Tony. Jan. 21, 2016. Plant Delights Nursery—Perennials—New, Exciting and Overlooked. http://www.scnla.com/SCHI_2016_Presentations/TonyAvantHandout.pdf. 1 page.*

* cited by examiner

*Primary Examiner* — Susan McCormick Ewoldt
*Assistant Examiner* — Karen M Redden

(57) ABSTRACT

A new and unique ×*Mangave* plant named 'Moonglow' characterized by narrow, slightly arching succulent foliage of glaucous, silvery blue-green developing very large, dark, greyed-purple spots. The waxy, light green and yellow flowers on tall, stiff, lightly branched scapes are loaded with nectar are highly attractive to hummingbirds.

1 Drawing Sheet

Botanical classification: ×*Mangave* times *Manfreda* hybrid.

Variety denomination: 'Moonglow'.

BACKGROUND OF THE INVENTION

The present invention relates to the new and distinct ×*Mangave* plant, ×*Mangave* 'Moonglow' hybridized by the inventor at a wholesale perennial nursery in Zeeland, Mich., USA as part of an intense breeding program crossed in Dec. 26, 2011. Seed was harvested on Aug. 8, 2012. Through growing trials at the same nursery the new plant was referred to by the breeder code 12-08-01. The new plant has been successfully asexually propagated initially by division at the same nursery in Zeeland, Mich. and also by sterile shoot tip tissue culture. Both methods of asexual propagation systems have been found to produce stable and identical plants that maintain all the unique characteristics of the original plant.

No plants of ×*Mangave* 'Moonglow' have been sold, in this country or anywhere in the world, prior to the filing of this application, nor has any disclosure of the new plant been made prior to the filing of this application with the exception of that which was disclosed within one year of the filing of this application, and was either derived directly or indirectly from the inventor.

BRIEF SUMMARY OF THE INVENTION

×*Mangave* 'Moonglow' differs from its parents as well as all other *Manfreda, Agave* and ×*Mangave* known to the applicant. The most similar known cultivar are 'Pineapple Express' U.S. Plant patent application Ser. No. 14/999,084 and the female parent ×*Mangave* 'Bloodspot' (not patented). Compared to 'Pineapple Express' the new plant has longer leaves that project more outward and not as upward as 'Pineapple Express', and the new plant is also more silvery in foliage color with much larger dark, greyed-purple spots that overlap. Compared to the female parent, 'Bloodspot', the new plant has larger dark grey-purple spots on the foliage that has less noticeable marginal dentation and without as pronounced burgundy margins. In addition, 'Bloodspot' has thicker leaves and grows slower than the new plant. Compared to the male parent, 'Chocolate Chip' (not patented), the new plant has shorter leaves that are flatter and less sinuate with larger, dark, greyed-purple spots.

The new plant, 'Moonglow', is unique from these and all other *Agave,* ×*Mangave* and *Manfreda* known to the inventor by the following combined traits:

1. Narrow, mostly-flat, slightly-arching, succulent foliage of glaucous, silvery blue-green.
2. Sessile foliage develops large, overlapping dark, greyed-purple spots with direct ultra violet light exposure;
3. Rapid growth rate with good natural pup production;
4. Waxy flowers of light green and yellow on stiff, tall, lightly-branched stapes.

BRIEF DESCRIPTION OF THE DRAWINGS

The photograph of the new plant demonstrates the overall appearance of the new plant including the unique traits as a two-year-old plant grown in a container in a heated greenhouse in Zeeland, Mich. with supplemental water and fertilizer as needed. The colors are as accurate as reasonably possible with color reproductions. Ambient light spectrum, temperature, source and direction may cause the appearance of minor variation in color.

DETAILED BOTANICAL DESCRIPTION

Figure 1:
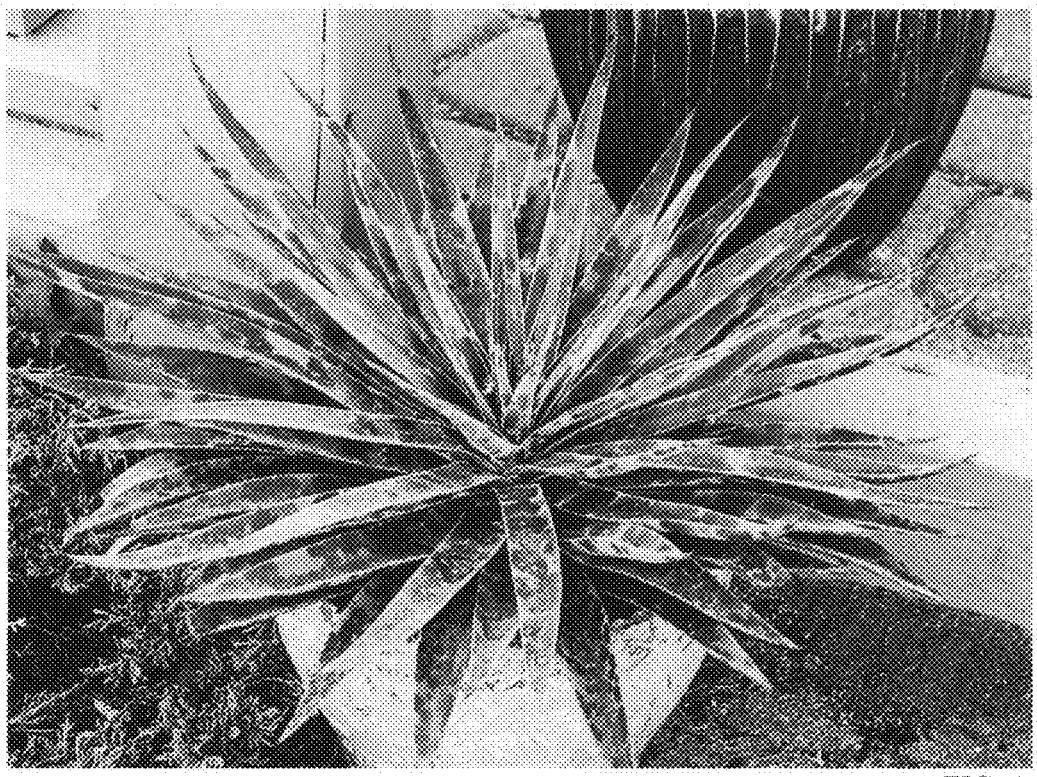
FIG. 1 shows the new plant in a container prior to flowering.
Figure 2:
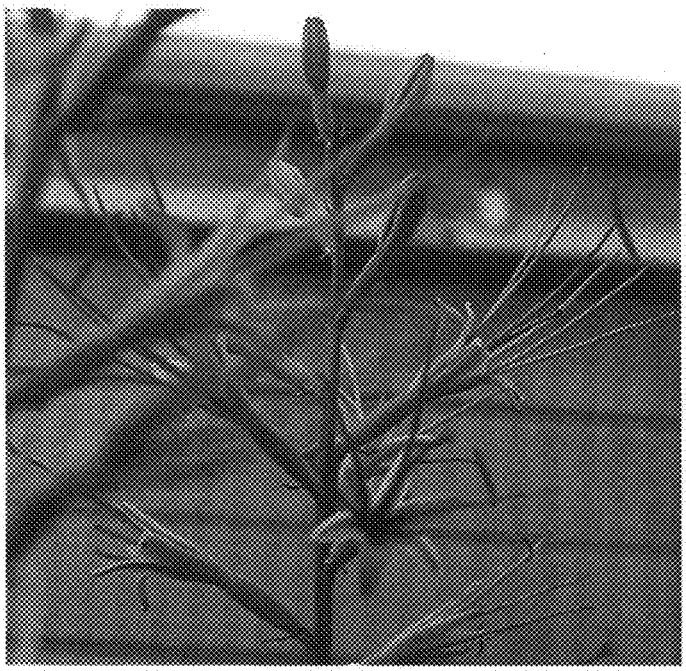
FIG. 2 shows a close-up of the flowers and buds.

The following descriptions and color references are based on The 2001 edition of The Royal Horticultural Society Colour Chart except where common dictionary terms are used. The new plant, ×*Mangave* 'Moonglow', has not been observed under all possible environments. The phenotype may vary slightly with different environmental conditions, such as temperature, light, fertility, moisture and maturity levels, but without any change in the genotype. The following observations and size descriptions are of a two-year old plant in a commercial wholesale greenhouse in Zeeland, Mich. with supplemental water and fertilizer as needed.

Botanical classification: ×*Mangave* hybrid.

Variety denomination: 'Moonglow'.

Female (seed) parent: ×*Mangave* 'Bloodspot'.

Male (pollen) parent: *Manfreda* 'Chocolate Chip'.

Propagation: Division and sterile plant tissue culture.

Time to initiate roots from tissue culture: About 21 days.

Growth rate: Moderate to rapid.

Crop time: About 12 to 16 weeks to finish during lengthening spring days and warm summer days from an established 25 mm tissue culture plug to a 65 mm diameter container.

Rooting habit: Fleshy, lightly branching, with roots up to 15 cm long.

Root color: Nearest RHS 158C.

Plant shape and habit: Succulent herbaceous perennial with basal rosettes of about 80 fleshy leaves radially emerging and slightly arching from central rhizome, producing a low, symmetrical, rounded, mound.

Plant size: Foliage height about 17.0 cm tall from soil line to the top of the leaves and about 42.0 cm wide at the widest point at soil line.

Foliage description: Lanceolate; simple, fleshy, very glabrous; margins finely dentate with short flexible teeth; apex acute with flexible mucro; base truncate, sessile, clasping.

Number of leaves: About 80 per plant.

Leaf blades: Finely dentate; to about 22.5 cm long, about 3.0 cm wide at base and 4.5 mm thick, average about 18.5 cm long, 2.5 cm wide and 4.0 mm thick; usually bi-laterally symmetrical; very glabrous and glaucous above and below; spotted with typically irregularly shaped and sized, overlapping, dark, greyed-purple spots.

Foliage fragrance: None observed.

Leaf blade color:

*Adaxial* (*young*).—Nearest RHS 138C with spots between RHS 137C and RHS 137D.

*Abaxial* (*young*).—Nearest RHS 193C with spots nearest RHS 191B.

*Adaxial* (*mature*).—Between RHS N187C and RHS 187D with a blend of RHS 115C and with overlapping spots of nearest RHS N187A.

*Abaxial* (*mature*).—Nearest RHS 146C with spots of nearest RHS 146A tinted with nearest RHS N186B.

Mucro: Flexible; straight, about 6.0 mm long.

Mucro color: Nearest RHS N199D.

Spine texture: Flexible, glabrous, sharply pointed.

Petiole: Sessile.

Veins: Parallel; not distinct.

Peduncle: Terete; very glaucous; glabrous; stiff; strong; with cauline leaves nearly adpressed along surface; about 170 cm long and 1.3 cm diameter at base; attitude upwards, erect.

Peduncle color: Basal region nearest RHS N187B, distal region nearest RHS 139A.

Pedicel: Terete; glaucous; glabrous; stiff; strong; about 1.2 cm long and 2.5 mm diameter; outwardly to slightly upright.

Pedicel color: Nearest RHS 139A.

Cauline leaves: About 30 per scape; lanceolate; simple, fleshy, glabrous; margins finely dentate with flexible teeth; apex acute with mucro; base truncate, sessile, clasping; proximally about 11.5 cm long and about 1.5 cm wide at base, decreasing distally; color adaxial and abaxial same as basal leaves.

Buds one day prior to opening: Tubular base with terminal elongated ellipsoid; terminal ellipsoid about 2.2 cm long and about 1.0 cm across; proximal tube about 2.0 cm long and 6.0 mm across; overall about 4.2 cm long.

Bud color: Nearest RHS 138A.

Flower description: Perfect, actinomorphic; about 9.0 cm long and opening to about 4.7 cm across at outside of anthers; lasting about 3 to 4 days per flower; flowering period about three weeks in late winter in Michigan greenhouse; producing abundant nectar; approximately 75 flowers per scape; outwardly to slightly upright.

Flower fragrance: Faintly sweet.

Tepals: Six; glaucous abaxial; glabrous both adaxial and abaxial; acute apex and fused base; in two sets of three; outer set about 2.6 cm long and about 5.0 mm wide at base; inner set about 2.6 cm long and 4.0 mm wide at base; inner set creased along edge where overlapped with outer set while in bud.

Tepal color: Outer set adaxial nearest RHS 160B with speckling of nearest RHS 183B, abaxial nearest RHS N138C with glaucous bloom and nearest RHS 138A with glaucous bloom removed; inner set adaxial longitudinal center nearest RHS 160B with speckling of nearest RHS 183B and marginal 1.5 mm nearest RHS 151D, and abaxial longitudinal center nearest RHS N138C and blend between RHS 11B and RHS 151A along 1.5 mm wide margin.

Androecium: Six.

*Filaments*.—Six; stiff and straight; about 5.5 cm long and 2.0 mm diameter at base; color nearest RHS 159D with dense speckling of nearest RHS 182A.

*Anther*.—Dorsifixed; longitudinal; about 1.7 cm long and 2.0 mm diameter before opening; after dehiscence curving backward; color between RHS 178A and RHS 183B.

*Pollen*.—Abundant; color nearest RHS 18A.

Gynoecium: Single.

*Style*.—5.5 cm long and 2.0 mm diameter at base; color nearest RHS 185A undertones of nearest RHS 160D.

*Stigma*.—Globose, apex tri-lobed; about 2.5 mm tall and 3.0 mm across top; color side and top nearest RHS 187A; top stigmatic surface in tri-pointed star with color nearest RHS N187C.

*Ovary*.—Inferior.

Fruit: Dehiscent, tri-valved, oblong, loculicidal capsule; apex abruptly acute; base slightly tapered; about 3.3 cm long and 1.6 cm across.

Fruit color: When immature nearest RHS N138B; at dehiscence blend between RHS 199C and RHS 161B.

Seed: Flattened, near round; about 4.0 mm across and about 1.0 mm thick; color nearest RHS 202A.

Disease resistance: ×*Mangave* 'Moonglow' has not been observed to be resistant to diseases common to other ×*Mangave* beyond that which is normal for *Agave* or *Manfreda*. The plant is xeromorphic and survives well with minimal water once established. Hardiness at least from USDA zone 9 to 11. Full extent of winter hardiness has not been tested.

I claim:

1. A new and distinct cultivar of ornamental ×*Mangave* plant named 'Moonglow' as herein described and illustrated, suitable as a potted plant or for the landscape.

* * * * *